United States Patent
Fouqueray et al.

(10) Patent No.: US 9,271,984 B2
(45) Date of Patent: Mar. 1, 2016

(54) TREATMENT OF TYPE 1 DIABETES

(75) Inventors: Pascale Fouqueray, Sins (CH); Daniel Cravo, Montesson (FR); Sophie Hallakou-Bozec, Montrouge (FR); Sébastien Bolze, Massieux (FR)

(73) Assignee: POXEL, Lyon (FR)

( * ) Notice: Subject to any disclaimer, the term of this patent is extended or adjusted under 35 U.S.C. 154(b) by 0 days.

(21) Appl. No.: 13/703,147

(22) PCT Filed: Jun. 9, 2011

(86) PCT No.: PCT/EP2011/059589
§ 371 (c)(1),
(2), (4) Date: Feb. 2, 2013

(87) PCT Pub. No.: WO2011/154496
PCT Pub. Date: Dec. 15, 2011

(65) Prior Publication Data
US 2013/0131066 A1    May 23, 2013

(30) Foreign Application Priority Data

Jun. 9, 2010   (EP) .................................. 10305611

(51) Int. Cl.
*A01N 43/66* (2006.01)
*A61K 31/53* (2006.01)
*A61K 9/20* (2006.01)

(52) U.S. Cl.
CPC .............. *A61K 31/53* (2013.01); *A61K 9/2027* (2013.01); *A61K 9/2054* (2013.01)

(58) Field of Classification Search
None
See application file for complete search history.

(56) References Cited

U.S. PATENT DOCUMENTS

| 7,034,021 B2 * | 4/2006 | Moinet et al. ................. 514/245 |
| 7,452,883 B2 * | 11/2008 | Moinet et al. ................. 514/245 |
| 8,592,370 B2 * | 11/2013 | Mesangeau ............ A61K 31/53 514/241 |
| 2003/0109530 A1 | 6/2003 | Moinet et al. |
| 2006/0223803 A1 | 10/2006 | Moinet et al. |
| 2008/0108619 A1 * | 5/2008 | Moinet et al. ................. 514/241 |

FOREIGN PATENT DOCUMENTS

| WO | WO 01/55122 | 8/2001 |
| WO | WO 2004/089917 | 10/2004 |
| WO | WO 2010/066326 | 6/2010 |
| WO | WO 2010066901 A2 * | 6/2010 ........... C07D 251/10 |

OTHER PUBLICATIONS

CAS RN: 91-76-9 (Entered STN Nov. 16, 1984).*

(New England Journal of Medicine Article) DCCT/EDIC Study, "Intensive Diabetes Treatment and Cardiovascular Disease in Patients with Type 1 Diabetes," N Engl J Med 2005; vol. 353, No. 25, :2643-2653.*
Pozzilli et al., "Autoimmune Diabetes Not Requiring Insulin at Diagnosis (Latent Autoimmune Diabetes of the Adult)," Diabetes Care, vol. 24, No. 8, Aug. 2001.*
Schram et al., "Advanced Glycation End Products are Associated With Pulse Pressure in Type 1 Diabetes," Hypertension, 2005;46:232-237.*
Katakami et al., "Decrease Endogenous Secretory Advanced Glycation End Product Receptor in Type 1 Diabetic Patients," Diabetes Care, vol. 28, No. 11, Nov. 2005.*
Winter et al., "Immunological Markers in the Diagnosis and Prediction of Autoimmune Type 1a Diabetes," Clinical Diabetes, vol. 20, No. 4, 2002.*
International Search Report for PCT/EP2011/059589, mailed Sep. 20, 2011, Giacobbe, Simone.
Written Opinion of the International Searching Authority for PCT/EP2011/059589, mailed Sep. 20, 2011, Giacobbe, Simone.
Declaration Under Rule 132 executed by Dr. Sophie Hallakou-Bozec on May 21, 2015.
Declaration Under Rule 132 executed by Dr. Etienne Larger on May 22, 2015.
Sosenko et al, "A Risk Score for Type 1 Diabetes Derived From Autoantibody-Positive Participants in the Diabetes Prevention Trial-Type 1", Diabetes Care, vol. 31, No. 3, pp. 528-533, Mar. 2008.
Ziegler et al, "Seroconversion to Multiple Islet Autoantibodies and Risk of Progression to Diabetes in Children", JAMA, vol. 309, No. 23, pp. 2473-2479, Jun. 19, 2013.
Krischer et al, "Screening Strategies for the Identification of Multiple Antibody-Positive Relatives of Individuals with Type 1 Diabetes", The Journal of Clinical Endocrinology & Metabolism 881(1):103-108, 2003.
Simmons et al, "Type 1 diabetes: A predictable disease", World J. Diabetes Apr. 15, 2015; 6(3):380-390.
Baumann, "Anti-inflammatory therapy in type 1 diabetes", Curr Diab Rep. Oct. 2012; 12(5):499-509, Abstract.

* cited by examiner

*Primary Examiner* — Craig Ricci
*Assistant Examiner* — Jared D Barsky
(74) *Attorney, Agent, or Firm* — Nixon & Vanderhye P.C.

(57) ABSTRACT

The present invention relates to triazine derivatives of formula (I) for their use in the treatment of type 1 diabetes mellitus, and to compositions comprising said triazine derivatives.

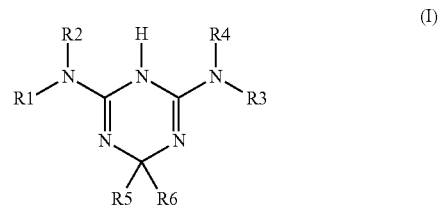

5 Claims, 1 Drawing Sheet

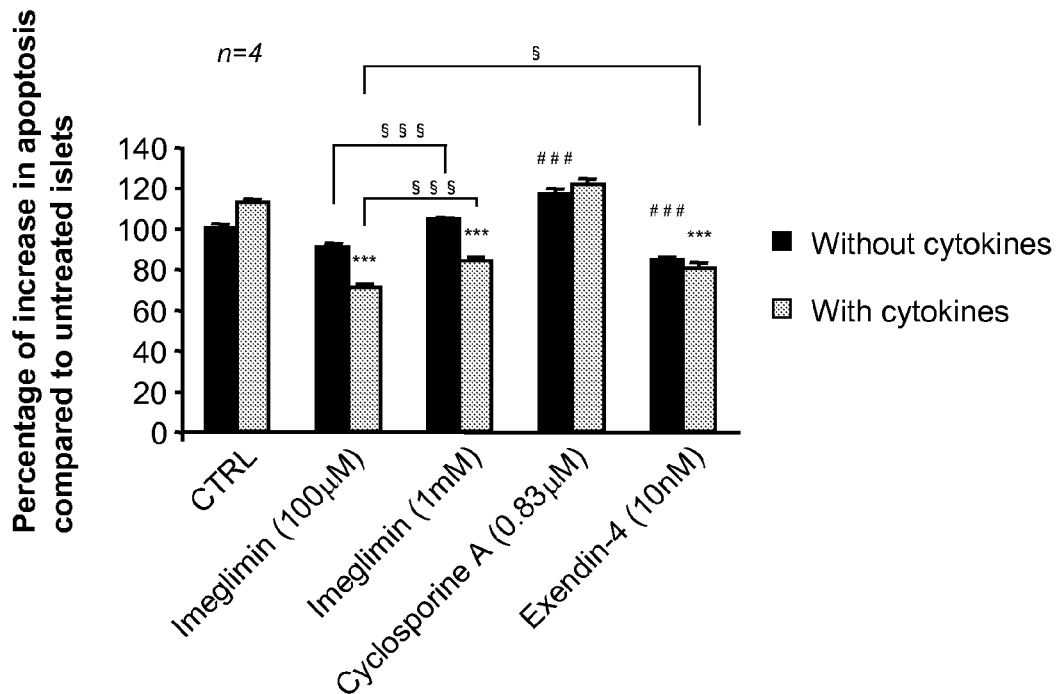

TREATMENT OF TYPE 1 DIABETES

This application is the U.S. national phase of International Application No. PCT/EP2011/059589, filed 9 Jun. 2011, which designated the U.S. and claims priority to EP Application No. 10305611.5, filed 9 Jun. 2010, the entire contents of each of which are hereby incorporated by reference.

The present invention relates to triazine derivatives or composition comprising the same for their use in the treatment of type 1 diabetes mellitus, in particular to delay the onset of type 1 diabetes or slow down its progression.

BACKGROUND

Diabetes mellitus is a chronic metabolic disorder of multiple aetiology, characterized by chronic hyperglycemia with disturbance of carbohydrate, fat and protein metabolism resulting from defects in insulin secretion, insulin action, or both. The effect of diabetes mellitus includes long-term damage, dysfunction and failure of various organs. Diabetes mellitus is usually divided into two major categories:

Type 1 diabetes (formerly insulin-dependent diabetes mellitus) encompasses the majority of cases which are primarily due to pancreatic islet beta cell destruction, usually develop in childhood or adolescence and are prone to ketosis and acidosis. Type 1 diabetes accounts for around 10% of all diabetes.

Type 2 diabetes (formerly non insulin-dependent diabetes mellitus) includes the common major form of diabetes which results from defect(s) in insulin secretion, almost always with a major contribution from insulin resistance. Type 2 diabetes accounts for around 90% of all diabetes.

The onset of symptoms in type 1 diabetes is usually acute and frequently follows an antecedent viral infection which might be the trigger to a process leading to destruction of beta cells secondary to auto immune insulitis. When beta cells destruction reaches the critical point, the patient's reduced insulin levels lead to hyperglycaemia with the typical symptomatology of type 1 diabetes.

Type 1 diabetes can affect many major organs, including heart, blood vessels, nerves, eyes and kidneys leading to cardiovascular diseases, retinopathy (up to blindness), neuropathy and nephropathy (up to dialysis). Adequate control of blood glucose concentration can dramatically reduce the risk of many complications. The main treatment regimen for type 1 diabetes involves administration of insulin, usually subcutaneously. There are different regimens for insulin therapy, and various combinations of long acting, intermediate and short acting insulins can be used depending on the context. Continuous insulin delivery using a pump can also be used to accurately control blood glucose concentration. The more intensive regimens tend to provide better control of blood glucose, however they are much more intrusive to the patient's life, which can be a particular problem when treating juveniles with this condition.

SUMMARY OF THE INVENTION

In view of the unsatisfactory prognosis for patients with type 1 diabetes, it would be advantageous to have an alternative treatment which could be used instead of insulin. In particular, it would be especially advantageous to have a treatment able to delay the onset of type 1 diabetes or slow down its progression, especially at early stages, where beta cells destruction has not reached the critical point yet. The inventors have unexpectedly discovered that triazine derivatives were efficient at protecting beta cells from cellular death, and could consequently be useful in the treatment of type 1 diabetes. This would be an help to prevent further beta cell death once the diagnosis of type 1 diabetes has been performed, (or to try to preserve as much as possible beta cell mass which has not been yet destroyed by the autoimmune process) or to prevent or delay beta cell death in at risk population before the stage of type 1 diabetes (for instance in relatives of type 1 diabetes subjects with positive antibodies).

International patent application WO2001/055122 describes triazine derivatives and their hypoglycaemic properties. To our knowledge, the activity of such triazine derivatives in protecting beta cells from destruction and their use in the treatment of type 1 diabetes have never been described.

BRIEF DESCRIPTION OF THE FIGURES

FIG. 1: Percentage of increase in apoptosis compared to untreated rat islets (set to 100%). Values represent the mean+/−sem of four independent experiments in duplicate. Islets from six rats were pooled for each experiment. §$P<0.05$ and §§§$P<0.001$. ### $P<0.001$ when specifically compared to control without cytokines. ***$P<0.001$ when specifically compared to control with cytokines.

DETAILED DESCRIPTION OF THE INVENTION

The first object of the present invention is a triazine derivative according to formula (I) for its use in the treatment of type 1 diabetes.

The triazine derivative according to the invention is a compound of formula (I):

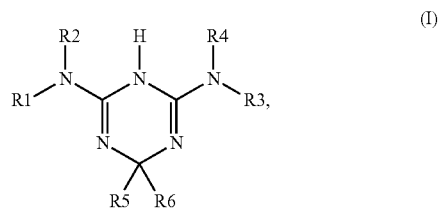

wherein:

R1, R2, R3 and R4 are independently chosen from the following groups:

H, (C1-C20)alkyl optionally substituted by halogen, (C1-C5) alkyl, (C1-C5)alkoxy or (C3-C8)cycloalkyl, (C2-C20)alkenyl optionally substituted by halogen, (C1-C5)alkyl or (C1-C5)alkoxy, (C2-C20)alkynyl optionally substituted by halogen, (C1-C5)alkyl or (C1-C5)alkoxy, (C3-C8)cycloalkyl optionally substituted by (C1-C5)alkyl or (C1-C5)alkoxy, hetero(C3-C8)cycloalkyl bearing one or more heteroatoms chosen from N, O and S and optionally substituted by (C1-C5)alkyl or (C1-C5)alkoxy, (C6-C14)aryl(C1-C20)alkyl optionally substituted by amino, hydroxyl, thio, halogen, (C1-C5)alkyl, (C1-C5) alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl, (C6-C14)aryl optionally substituted by amino, hydroxyl, thio, halogen, (C1-C5)alkyl, (C1-C5)alkoxy, (C1-C5) alkylthio, (C1-C5)alkylamino, (C6-C14)aryloxy, (C6-

C14)aryl(C1-C5)alkoxy, cyano, trifluoromethyl, carboxyl, carboxymethyl or carboxyethyl, (C1-C13)heteroaryl bearing one or more heteroatoms chosen from N, O and S and optionally substituted by amino, hydroxyl, thio, halogen, (C1-C5)alkyl, (C1-C5) alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl, R1 and R2, on the one hand, and R3 and R4, on the other hand, possibly forming with the nitrogen atom to which they are linked an n-membered ring (n between 3 and 8) optionally containing one or more heteroatoms chosen from N, O and S and possibly being substituted by one or more of the following groups: amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl, R5 and R6 are independently chosen from the following groups:

H, (C1-C20)alkyl optionally substituted by amino, hydroxyl, thio, halogen, (C1-C5)alkyl, (C1-C5)alkoxy, (C1-C5) alkylthio, (C1-C5)alkylamino, (C6-C14)aryloxy, (C6-C14)aryl(C1-C5)alkoxy, cyano, trifluoromethyl, carboxyl, carboxymethyl or carboxyethyl, (C2-C20)alkenyl optionally substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl, (C2-C20)alkynyl optionally substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl, (C3-C8)cycloalkyl optionally substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl, hetero(C3-C8)cycloalkyl bearing one or more heteroatoms chosen from N, O and S and optionally substituted by amino, hydroxyl, thio, halogen, (C1-C5)alkyl, (C1-C5) alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl, (C6-C14)aryl optionally substituted by amino, hydroxyl, thio, halogen, (C1-C5)alkyl, (C1-C5)alkoxy, (C1-C5) alkylthio, (C1-C5)alkylamino, (C6-C14)aryloxy, (C6-C14)aryl(C1-C5)alkoxy, cyano, trifluoromethyl, carboxyl, carboxymethyl or carboxyethyl, (C1-C13)heteroaryl bearing one or more heteroatoms chosen from N, O and S and optionally substituted by amino, hydroxyl, thio, halogen, (C1-C5)alkyl, (C1-C5) alkoxy, (C1-C5)alkylthio, (C1-C5)alkylamino, (C6-C14)aryloxy, (C6-C14)aryl(C1-C5)alkoxy, trifluoromethyl, carboxyl, carboxymethyl or carboxyethyl, (C6-C14)aryl(C1-C5)alkyl optionally substituted by amino, hydroxyl, thio, halogen, (C1-C5)alkyl, (C1-C5) alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl, R5 and R6 possibly forming with the carbon atom to which they are attached an m-membered ring (m between 3 and 8) optionally containing one or more heteroatoms chosen from N, O and S and possibly being substituted by amino, hydroxyl, thio, halogen, (C1-C5)alkyl, (C1-C5) alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl, or possibly forming with the carbon atom a C10-C30 polycyclic residue optionally substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl (C1-C5) alkoxy, cyano, trifluoromethyl, carboxyl, carboxymethyl or carboxyethyl, R5 and R6 together also possibly representing the group =O or =S, the nitrogen atom of a heterocycloalkyl or heteroaryl group possibly being substituted by a (C1-C5)alkyl, (C3-C8)cycloalkyl, (C6-C14)aryl, (C6-C14) aryl(C1-C5) alkyl or (C1-C6)acyl group, a racemic form, tautomer, enantiomer, diastereoisomer, epimer or pharmaceutically acceptable salt thereof, or a mixture thereof.

In a particular embodiment, R5 is a hydrogen atom.

In a more particular embodiment, R6 is a methyl group and R5 is a hydrogen atom.

In another particular embodiment, R5 and R6 form with the carbon atom to which they are attached an m-membered ring (m between 3 and 8) optionally containing one or more heteroatoms chosen from N, O and S and possibly being substituted by one or more of the following groups: (C1-C5)alkyl, amino, hydroxyl, (C1-C5)alkylamino, alkoxy(C1-C5), (C1-C5)alkylthio, (C6-C14)aryl, (C6-C14) aryl(C1-C5)alkoxy.

In a more particular embodiment, R5 and R6 form with the carbon atom to which they are attached a C10-C30 polycyclic residue optionally substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5) alkoxy, cyano, trifluoromethyl, carboxyl, carboxymethyl or carboxyethyl.

In another particular embodiment, R5 and R6 are independently chosen from (C1-C20)alkyl groups optionally substituted by amino, hydroxyl, thio, halogen, (C1-C5)alkyl, (C1-C5)alkoxy, (C1-C5)alkylthio, (C1-C5)alkylamino, (C6-C14) aryloxy, (C6-C14)aryl(C1-C5)alkoxy, cyano, trifluoromethyl, carboxyl, carboxymethyl or carboxyethyl groups.

In a particular embodiment, R1, R2, R3 and R4 are independently chosen from H and (C1-C20)alkyl groups optionally substituted by halogen, (C1-C5)alkyl, (C1-C5)alkoxy or (C3-C8)cycloalkyl; preferably, R1=R2=H and R3=R4=(C1-C20)alkyl optionally substituted by halogen, (C1-C5)alkyl, (C1-C5)alkoxy or (C3-C8)cycloalkyl.

In a particular embodiment, R5 and R6 are independently chosen from H and (C1-C20)alkyl groups optionally substituted by amino, hydroxyl, thio, halogen, (C1-C5)alkyl, (C1-C5)alkoxy, (C1-C5)alkylthio, (C1-C5)alkylamino, (C6-C14) aryloxy, (C6-C14)aryl(C1-C5)alkoxy, cyano, trifluoromethyl, carboxyl, carboxymethyl or carboxyethyl groups; more preferably, R5=H and R6=(C1-C20)alkyl optionally substituted by amino, hydroxyl, thio, halogen, (C1-C5)alkyl, (C1-C5)alkoxy, (C1-C5)alkylthio, (C1-C5) alkylamino, (C6-C14)aryloxy, (C6-C14)aryl(C1-C5)alkoxy, cyano, trifluoromethyl, carboxyl, carboxymethyl or carboxyethyl groups.

In a preferred embodiment, R1 and R2 are methyl groups and R3 and R4 are hydrogen atoms.

A preferred family of compounds of formula (I) includes compounds wherein R1, R2 and R6 are, independently of each other, (C1-C20)alkyl groups and R3, R4 and R5 are hydrogen atoms. In particular, R1, R2 and R6 are methyl groups.

The term "m-membered ring" formed by R5 and R6 means in particular a saturated ring, such as a cyclohexyl, piperidyl or tetrahydropyranyl group. The term "polycyclic group" formed by R5 and R6 means an optionally substituted carbon-based polycyclic group, and in particular a steroid residue.

Compounds of the formula (I) that may especially be mentioned include:

| | Formula | Salt |
|---|---|---|
| 1 | [structure: triazine with N(CH$_3$)$_2$, NH$_2$, and ethyl substituents] | HCl |
| 2 | [structure: triazine with two N(CH$_3$)H-CH$_3$ groups and CH$_3$] | HCl |
| 3 | [structure: triazine with N(CH$_3$)$_2$, NH$_2$, and two CH$_3$ groups] | |
| 4 | [structure: triazine with N(CH$_3$)$_2$, NH$_2$, spiro-cyclohexyl] | HCl |
| 5 | [structure: triazine with N(CH$_3$)$_2$, NH$_2$, and two CH$_3$ groups] | Methanesulfonate |
| 6 | [structure: triazine with N(CH$_3$)$_2$, NH$_2$, CH$_3$ and propyl-OH] | |
| 7 | [structure: triazine with N(CH$_3$)$_2$, NH$_2$, CH$_3$ and propyl-OH] | HCl |

| | Formula | Salt |
|---|---|---|
| 8 | (4,6-bis-dimethylamino-dihydrotriazine with N-allyl, gem-dimethyl) | HCl |
| 9 | (4,6-bis-dimethylamino-dihydrotriazine with N-isopropyl, gem-dimethyl) | HCl |
| 10 | (dimethylamino-amino-dihydrotriazine with phenyl) | HCl |
| 11 | (dimethylamino-amino-dihydrotriazine with 4-methoxyphenyl) | HCl |
| 12 | (dimethylamino-amino-dihydrotriazine with 4-hydroxyphenyl) | HCl |

| | Formula | Salt |
|---|---|---|
| 13 | 2-(4-hydroxyphenyl)-N4,N4,N6-trimethyl-2,5-dihydro-1,3,5-triazine-4,6-diamine | |
| 14 | N2-ethyl-N4,N4,6,6-tetramethyl-1,6-dihydro-1,3,5-triazine-2,4-diamine | Fumarate |
| 15 | N2,N2,N4,N4,6,6-hexamethyl-1,6-dihydro-1,3,5-triazine-2,4-diamine | HCl |
| 16 | N2,N2,N4,6,6-pentamethyl-1,6-dihydro-1,3,5-triazine-2,4-diamine | HCl |
| 17 | N,N,4,4-tetramethyl-6-(pyrrolidin-1-yl)-1,4-dihydro-1,3,5-triazin-2-amine | HCl |
| 18 | N4,N4,6-trimethyl-2,5-dihydro-1,3,5-triazine-2,4-diamine | HCl |

-continued

| | Formula | Salt |
|---|---|---|
| 19 | | HCl |
| 20 | | Carbonate |
| 21 | | Carbonate |
| 22 | | HCl |
| 23 | | HCl |
| 24 | | HCl |

-continued
| | Formula | Salt |
|---|---|---|
| 25 | 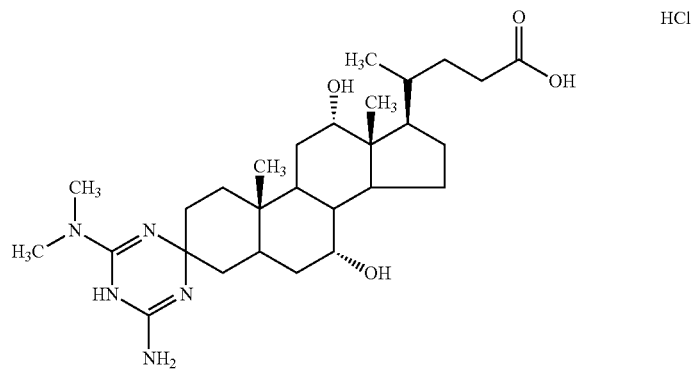 | HCl |
| 26 | 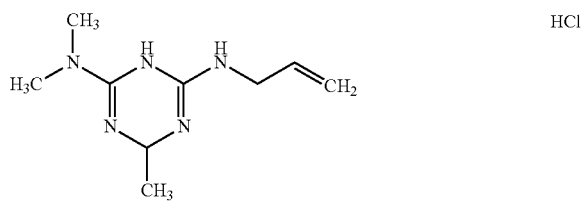 | HCl |
| 27 | 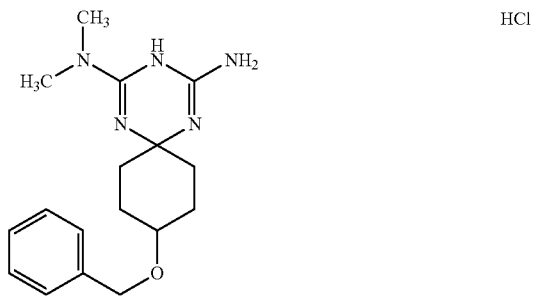 | HCl |
| 28 | 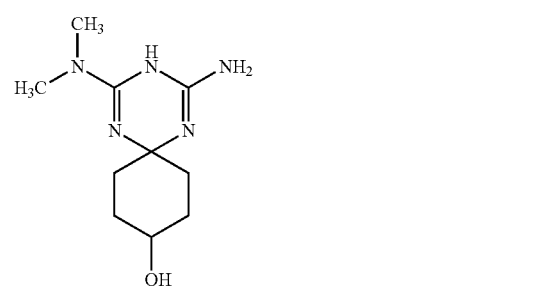 [SMILES: CN(C)C1=NC2(CCC(O)CC2)N=C(N)N1] | HCl |
| 29 | 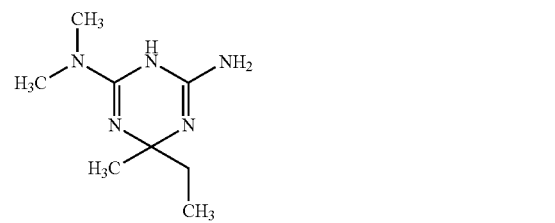 | Carbonate |

-continued

| | Formula | Salt |
|---|---|---|
| 30 | [structure: 6-membered ring with N-CH3/H3C, NH, NH2, N, N, C(CH2CH3)(CH2CH3)] | Carbonate |
| 31 | [structure: triazine spiro-fused with cyclopentane, N(CH3)(H3C), NH, NH2] | HCl |
| 32 | [structure: triazine with N(CH3)(H3C), NH, NH2, CH(CH2CH2CH3)] | Carbonate |
| 33 | [structure: triazine with N(CH3)(H3C), NH, NH2, CH2] | HCl |
| 34 | [structure: triazine with N(CH3)(H3C), NH, NH2, CH-cyclohexyl] | para-toluene-sulfonate |
| 35 | [structure: triazine with N(CH3)(H3C), NH, NH2, C(CH3)(CH3)] | HCl |
| 36 | [structure: triazine with N(CH3)(H3C), NH, NH2, CH-CF3] | para-toluene-sulfonate |

-continued

| | Formula | Salt |
|---|---|---|
| 37 | 6-benzyl-N2,N2-dimethyl-1,6-dihydro-1,3,5-triazine-2,4-diamine | para-toluene-sulfonate |
| 38 | N2,N2-dimethyl-9-oxa-1,3,5-triazaspiro[5.5] structure | HCl |
| 39 | N2,N2-dimethyl-9-methyl-1,3,5,9-tetraazaspiro[5.5] structure | HCl |
| 40 | 6-(furan-2-yl)-N2,N2-dimethyl-1,6-dihydro-1,3,5-triazine-2,4-diamine | HCl |
| 41 | N2,N2-dimethyl-6-(phenoxymethyl)-1,6-dihydro-1,3,5-triazine-2,4-diamine | para-toluene-sulfonate |
| 42 | 6-tert-butyl-N2,N2-dimethyl-1,6-dihydro-1,3,5-triazine-2,4-diamine | HCl |

-continued

| | Formula | Salt |
|---|---|---|
| 43 | (structure: 2-amino-4-dimethylamino-6-isobutyl-1,3,5-triazine, dihydro) | HCl |
| 44 | (structure: 2-amino-4-dimethylamino-6-isopropyl-1,3,5-triazine, dihydro) | HCl |
| 45 | (structure: 2-amino-4-dimethylamino-6-(cyclohex-3-enyl)-1,3,5-triazine, dihydro) | para-toluene-sulfonate |

In the above table, absence of mention of the salt nature means that the considered compound is the free amine.

In a preferred embodiment, the triazine derivative of formula (I) is chosen from 2-amino-3,6-dihydro-4-dimethylamino-6-methyl-1,3,5-triazine, a racemic form, tautomer, enantiomer, diastereoisomer and epimer thereof, and a pharmaceutically acceptable salt thereof.

In a preferred embodiment, the triazine derivative of formula (I) is chosen from (+)-2-amino-3,6-dihydro-4-dimethylamino-6-methyl-1,3,5-triazine and a pharmaceutically acceptable salt thereof.

In a preferred embodiment, the triazine derivative of formula (I) is chosen from (−)-2-amino-3,6-dihydro-4-dimethylamino-6-methyl-1,3,5-triazine and a pharmaceutically acceptable salt thereof.

In a highly preferred embodiment, the triazine derivative of formula (I) is (+)-2-amino-3,6-dihydro-4-dimethylamino-6-methyl-1,3,5-triazine hydrochloride.

In the present description, the terms used have, unless otherwise indicated, the following meanings:
- "alkyl" denotes a linear or branched saturated hydrocarbon radical. Among (C1-C20)alkyl radicals may be cited methyl, ethyl, propyl, isopropyl, butyl, sec-butyl, tert-butyl, pentyl, hexyl, octyl, decyl, dodecyl, hexadecyl and octadecyl radicals;
- "alkenyl" denotes a linear or branched hydrocarbon-based radical containing at least one double bond. Among (C1-C20)alkenyl radicals may be cited ethenyl, prop-2-enyl, but-2-enyl, but-3-enyl, pent-2-enyl, pent-3-enyl and pent-4-enyl radicals;
- "alkynyl" denotes a linear or branched hydrocarbon-based radical containing at least one triple bond. Among (C1-C20)alkynyl radicals may be cited ethynyl, prop-2-ynyl, but-2-ynyl, but-3-ynyl, pent-2-ynyl, pent-3-ynyl and pent-4-ynyl radicals;
- "halogen" refers for instance to fluorine, chlorine or bromine;
- "hydroxyl" refers to a —OH radical, "thio" to a —SH radical, "cyano" to a —CN radical, "trifluoromethyl" to a $CF_3$ radical, "carboxyl" to a —COOH radical, caboxymethyl to a —COOCH$_3$ radical and carboxyethyl to a —COOC$_2$H$_5$ radical;
- "alkoxy" refers to a —O-alkyl radical;
- "alkylthio" refers to a —S-alkyl radical;
- "alkylamino refers to a —NH-alkyl radical;
- "aryl" refers to a monocyclic or polycyclic hydrocarbon aromatic group, with at least one of the rings having a system of conjugated pi electrons, and including biaryls, which may be optionally substituted. Among (C6-C14) aryl groups may be cited biphenyl, phenyl, naphthyl, anthryl and phenanthryl radicals;
- "aryloxy" refers to a —O-aryl radical;
- "(C6-C14)aryl(C1-C20)alkyl" refers to the corresponding arylalkyl groups. Among (C6-C14)aryl(C1-C20)alkyl groups may be cited benzyl and phenethyl groups;
- "hetero(C6-C14)aryl" refers to a 6 to 14-membered aromatic heterocycle containing from 1 to 4 heteroatoms, the other atoms being carbon atoms. The heteroatoms can be oxygen, sulfur or nitrogen atoms. Among heteroaryl radicals may be cited furyl, thienyl, pyridyl, pyrrolyl, pyrimidyl, pyrazinyl, oxazolyl, oxadiazolyl, isoxazolyl, quinolyl and thiazolyl radicals;

"cycloalkyl" refers to a saturated hydrocarbon-based monocyclic or polycyclic ring. Among (C3-C8)cycloalkyl radicals may be cited cyclopropyl and cyclobutyl radicals.

The compounds of the present invention may contain asymmetric centres. These asymmetric centres may be, independently, in R or S configuration. It will be clear to a person skilled in the art that certain compounds that are useful according to the invention may also exhibit geometrical isomerism. It should be understood that the present invention includes individual geometrical isomers and stereoisomers and mixtures thereof, including racemic mixtures, of compounds of formula (I). Isomers of this type can be separated from mixtures thereof by application or adaptation of known processes, for example chromatography or recrystallisation techniques, or they can be prepared separately from suitable isomers of their intermediates.

Compounds of formula (I) also include the prodrugs of these compounds. The term "prodrugs" means compounds which, when administered to the patient, are chemically and/or biologically converted in the live body into compounds of formula (I). Enantiomers of the compounds according to the invention and the process for their preparation are especially described in patent application WO 2004/089917, the content of which is incorporated herein by reference.

The present patent application also concerns the polymorphic forms of the compounds, as obtained according to patent application WO 2004/089917, for instance the A1 or H1 polymorphic form of (+)-2-amino-3,6-dihydro-4-dimethylamino-6-methyl-1,3,5-triazine hydrochloride salts.

Triazine derivatives have been shown to be efficient at protecting beta cells from cellular death.

Another object of the present invention is the use of a triazine derivative of formula (I) as defined above in the preparation of a medicament for the treatment of type 1 diabetes.

Another object of the present invention is a pharmaceutical composition comprising at least one triazine derivative of formula (I) and a pharmaceutically acceptable support. The pharmaceutical composition comprising the triazine derivative of formula (I) according to the invention can be prepared by mixing the triazine derivative with a physiologically acceptable support, an excipient, a binder or a diluent. Preferably, the composition of the invention does not comprise insulin.

Another object of the present invention is the pharmaceutical composition of the invention for its use in the treatment of type 1 diabetes. Preferably, the patient in need of the treatment of the invention is not administered insulin in a range of time of less than 24 hours from (before or after) the administration of the composition of the invention.

Another object of the present invention is a method for treating type 1 diabetes comprising administration to a subject in need thereof of an effective amount of a triazine derivative of formula (I) or of a pharmaceutical composition comprising at least one triazine derivative of formula (I).

Within the context of the invention, the term treatment denotes curative, symptomatic, and/or preventive treatments. In particular, it can refer to reducing the progression of the disease, reducing or suppressing at least one of its symptoms or complications (including cardiovascular diseases, neuropathy, ulcers, retinopathy or nephropathy), or improving in any way the state of health of patients. The triazine derivatives of the invention can be used in humans with existing type 1 diabetes, including at early or late stages of the disease, preferably at early stage of the disease. The triazine derivatives of the invention can be used in humans to delay the onset of type 1 diabetes or slow down its progression. The derivatives of the invention will not necessarily cure the patient who has the disease but will delay or slow the progression or prevent further progression of the disease, ameliorating thereby the patient's condition. The derivatives of the invention can also be administered to those who do not have all symptoms of type 1 diabetes but who would normally develop the type 1 diabetes or be at increased risk for type 1 diabetes. Treatment also includes delaying the development of the disease in an individual who will ultimately develop all symptoms of type 1 diabetes or would be at risk for the disease due to age, familial history, genetic or chromosomal abnormalities, and/or due to the presence of one or more biological markers for the disease. By delaying the onset of the disease, derivatives of the invention prevent the individual from getting the disease during the period in which the individual would normally have gotten the disease or reduce the rate of development of the disease or some of its effects. Treatment also includes administration of the derivatives of the invention to those individuals thought to be predisposed to type 1 diabetes. In treating type 1 diabetes, the derivatives of the invention are administered in a therapeutically effective amount.

Cardiovascular diseases include more particularly high blood pressure, coronary artery disease, heart disease and/or stroke.

In the present invention, an "effective amount" is an amount sufficient to improve in any way the state of health of the patient.

The medicament for treating type 1 diabetes comprising a triazine derivative according to the invention is administrated to a subject in need thereof.

Subjects in need of such treatment may be divided into three categories.

First, some patients (group I) are "at risk" of developing type 1 diabetes; they present antibodies characteristic of the disease triggering. Beta cells of such patients may not be seriously damaged.

Second, the disease of some patients (group II) has been detected at an early stage of the disease. Beta cells of such patients may only be partially destroyed.

Third, some patients (group III) present a later form (evolved form) of type 1 diabetes.

Beta cells of such patients may be extensively damaged.

Patients of groups I and II are preferred patients to be treated according to the invention.

One aim of the treatment of the invention is in these groups of patients to delay progression of type 1 diabetes.

In a specific embodiment, subjects in need of the treatment of the invention are children or young subjects (in particular less than 30 years old) who suffer from type 1 diabetes. In another specific embodiment, subjects in need of the treatment of the invention are adults who suffer from LADA (Latent Autoimmune Diabetes of Adult). LADA is a form of type 1 diabetes which is diagnosed in individuals who are older than the usual age of onset of type 1 diabetes (that is, over 30 years of age at diagnosis). Alternate terms that have been used for "LADA" include Late-onset Autoimmune Diabetes of Adulthood, "Slow Onset Type 1" diabetes, and sometimes also "Type 1.5" diabetes. Patients with LADA are often mistakenly thought to have type 2 diabetes, based on their age at the time of diagnosis. LADA is described in P. Pozzilli et al. *Diabetes care* 2001, 24, 8, p. 1460-1467.

The amount of triazine derivative of formula (I) to be administered may evolve in a large scope depending upon the patient, the mode of administration and the expected effect. In particular, the amount of triazine derivative to be administered is comprised between 200 mg and 4000 mg, preferably between 500 and 3000 mg, in particular between 1000 and 2000 mg, per day.

Preferably, no insulin is administered to the patient less than 24 hours before or after the administration of the triazine derivative of formula (I) as described above.

In an embodiment, the triazine derivative is the only active principle in the composition of the invention.

The derivative or composition according to the invention can be administered orally or non-orally, for instance via parenteral, intravenous, cutaneous, nasal or rectal route.

The pharmaceutical composition of the invention can present different forms including granules, powders, tablets, gel capsules, syrups, emulsions, suspensions, and forms used for non-oral administration, for instance injections, sprays or suppositories. These pharmaceutical forms can be prepared via known conventional techniques.

The preparation of an orally administered solid pharmaceutical form can be for instance performed by the following process: an excipient (for example lactose, sucrose, starch or mannitol), a disintegrant (for example calcium carbonate, calcium carboxymethylcellulose, alginic acid, sodium carboxymethylcellulose, colloidal silicon dioxide, sodium croscarmellose, Crospovidone, guar gum, magnesium aluminium silicate, microcrystalline cellulose, cellulose powder, pregelatinised starch, sodium alginate or starch glycolate), a binder (for example alpha-starch, gum arabic, carboxymethylcellulose, polyvinylpyrrolidone, hydroxypropylcellulose, alginic acid, carbomer, dextrin, ethylcellulose, sodium alginate, maltodextrin, liquid glucose, magnesium aluminium silicate, hydroxyethylcellulose, methylcellulose or guar gum) and a lubricant (for example talc, magnesium stearate or polyethylene 6000) are added to the active principle and the mixture obtained is then tabletted. If necessary, the tablet can be coated via the known techniques, in order to mask the taste (for example with cocoa powder, mint, borneol or cinnamon powder) or to allow enteric dissolution or sustained release of the active principles. Coating products that can be used are, for example, ethylcellulose, hydroxymethylcellulose, polyoxyethylene glycol, cellulose acetophthalate, hydroxypropylmethylcellulose phthalate and Eudragit® (methacrylic acid-acrylic acid copolymer), Opadry® (hydroxypropylmethylcellulose+macrogol+titanium oxide+lactose monohydrate). Pharmaceutically acceptable colorants may be added (for example yellow iron oxide, red iron oxide or quinoline yellow lake).

Liquid pharmaceutical forms for oral administration include solutions, suspensions and emulsions. The aqueous solutions can be obtained by dissolving the active principle in water, followed by addition of flavourings, colorants, stabilisers and/or thickeners, if necessary. In order to improve the solubility, it is possible to add ethanol, propylene glycol or any other pharmaceutically acceptable non-aqueous solvent. The aqueous suspensions for oral use can be obtained by dispersing the finely divided active principle in water with a viscous product, such as a natural or synthetic gum or resin, methylcellulose or sodium carboxymethylcellulose.

The pharmaceutical forms for injection can be obtained, for example, by the following process. The active principle is dissolved, suspended or emulsified either in an aqueous medium (for example distilled water, physiological saline or Ringer's solution) or in an oily medium (for example olive oil, sesame seed oil, cottonseed oil, corn oil or propylene glycol), with a dispersant (for example Tween 80, HCO 60 (Nikko Chemicals), polyethylene glycol, carboxymethylcellulose or sodium alginate), a preserving agent (for example methyl p-hydroxybenzoate, propyl p-hydroxybenzoate, benzyl alcohol, chlorobutanol or phenol), an isotonicity agent (for example sodium chloride, glycerol, sorbitol or glucose) and optionally other additives, such as, if desired, a solubilising agent (for example sodium salicylate or sodium acetate) or a stabiliser (for example human serum albumin).

Pharmaceutical forms for external use can be obtained from a solid, semi-solid or liquid composition containing the active principle. For example, to obtain a solid form, the active principle can be treated with excipients (for example lactose, mannitol, starch, microcrystalline cellulose or sucrose) and a thickener (for example natural gums, cellulose derivatives or acrylic polymers) so as to convert them into powder. The liquid pharmaceutical compositions are prepared in substantially the same way as the forms for injection, as indicated previously. The semi-solid pharmaceutical forms are preferably in the form of aqueous or oily gels or in the form of pomades. These compositions may optionally contain a pH regulator (for example carbonic acid, phosphoric acid, citric acid, hydrochloric acid or sodium hydroxide) and a preserving agent (for example a p-hydroxybenzoic acid ester, chlorobutanol or benzalkonium chloride).

The triazine derivative according to the invention may be co-administered with at least one other active compound. Preferably, the at least one other active compound is different from insulin. Preferably, the at least one other active compound is chosen among treatments currently used to treat auto immune aggression. The term "co-administration" (or "co-administrered") means the simultaneous, separate or sequential administration of one or more compounds to the same patient, over a period that may be up to 2 hours or even up to 12 hours. For example, the term co-administration includes (1) a simultaneous administration of both compounds, (2) an administration of the first, followed 2 hours later by the administration of the second compound, (3) an administration of the first, followed 12 hours later by the administration of the second compound. In case insulin is co-administered with the triazine derivative of the invention, insulin is preferably administered to the patient more than 24 hours (preferably more than 25 hours) after the administration of the triazine derivative of formula (I) as described above.

The examples below are given as non-limiting illustrations of the invention.

EXAMPLES

Example 1

Study of the Protective Effect of a Triazine Derivative on Beta Cells Death

Rat pancreatic islets were cultured for 24 hours with or without a cocktail of cytokines (TNF-alpha, IL-1beta and INF-gamma each at 2 ng/ml), creating inflammatory stress, in order to quantify the protective properties of (+)-2-amino-3,6-dihydro-4-dimethylamino-6-methyl-1,3,5-triazine hydrochloride. Both doses of (+)-2-amino-3,6-dihydro-4-dimethylamino-6-methyl-1,3,5-triazine hydrochloride completely protected the islets from the cytokine stress.

These results allow concluding that (+)-2-amino-3,6-dihydro-4-dimethylamino-6-methyl-1,3,5-triazine hydrochloride has protective properties against basal and inflammation-like apoptosis on cultured rat islets.

Experimental Procedure:

Male Wistar rat islets (Elevage Janvier, Le Genest-St-Isle, France) were isolated using collagenase (Serva, Heidelberg, Germany) and cultured in RPMI at 11 mM glucose (Invitrogen, CA, USA) supplemented with 10% FCS (Fetal Calf Serum), 100 Units/ml penicillin, 100 µg/ml streptomycin and 100 µg/ml gentamycin in low-attachment 24-well plates (Corning, NY, USA). These islets were incubated with a cocktail of rat cytokines (TNF-alpha, IL-1beta and INF-gamma each at 2 ng/ml) for 24 hours (Brun T. et al., 2004 and 2007). 1 hour prior to cytokine incubation, (+)-2-amino-3,6-dihydro-4-dimethylamino-6-methyl-1,3,5-triazine hydrochloride (Imeglimin) at 100 µM or 1 mM, Cyclosporine A (CsA) at 0.83 µM or Exendin-4 (Exe-4) at 10 nM (Sigma, Mo., USA) was added separately to the medium to measure the protective effect of each drug on stressed or unstressed islets. Aliquots of the medium were used to measure insulin accumulated during the culture period using immune enzyme assay kits (Brunchwig, Basel, Switzerland). Furthermore, quantification of cytoplasmic nucleosomes, a direct indicator of apoptosis, was performed with the Cell Death Detection ELISA kit (Roche, Basel, Switzerland). Each condition was tested with 50 rat islets in duplicate and four independent experiments were performed. The results are provided as mean+/−sem and statistical analyses were performed using one-way ANOVA with Bonferroni and Dunnett post-hoc tests. The different conditions are summarized in the table below.

chloride at 100 µM had protective effects (10% less apoptosis than untreated islets). Cyclosporine A by itself induced a 17% increase in apoptosis. Exendin-4 showed the opposite effect with a 16% decrease in cell death. These results indicate that (+)-2-amino-3,6-dihydro-4-dimethylamino-6-methyl-1,3,5-triazine hydrochloride is by itself protective with a level of protection representing two thirds of the Exendin-4 level.

Cytokine treatment caused a 12% increase in cell death compared to untreated islets. In the presence of cytokines, (+)-2-amino-3,6-dihydro-4-dimethylamino-6-methyl-1,3,5-triazine hydrochloride at 100 µM had an even greater protective effect (37% less apoptosis than cytokine-stressed islets or 29% less apoptosis than untreated islets) while (+)-2-amino-3,6-dihydro-4-dimethylamino-6-methyl-1,3,5-triazine hydrochloride at 1 mM protected by 25% or 16% respectively. Cyclosporine A induced an 8% or 22% increase respectively, and Exendin-4 a drop of 29% or 20% in apoptosis. These values show a protective effect of (+)-2-amino-3,6-dihydro-4-dimethylamino-6-methyl-1,3,5-triazine hydrochloride. The lower concentration tested is nearly 50% more potent than Exendin-4.

| Condition # | 1 | 2 | 3 | 4 | 5 |
|---|---|---|---|---|---|
| Treatment of Islets | non-treated − cytokines | 100 µM Imeglimin − cytokines | 1 mM Imeglimin − cytokines | CsA 0.83 µM − cytokines | Exe-4 10 nM − cytokines |
| Nbr of Islets per duplicate | 50 | 50 | 50 | 50 | 50 |
| Condition # | 6 | 7 | 8 | 9 | 10 |
| Treatment of Islets | non-treated + cytokines | 100 µM Imeglimin + cytokines | 1 mM Imeglimin + cytokines | CsA 0.83 µM + cytokines | Exe-4 10 nM + cytokines |
| Nbr of Islets per duplicate | 50 | 50 | 50 | 50 | 50 |

Results:

To quantify the protective effect of (+)-2-amino-3,6-dihydro-4-dimethylamino-6-methyl-1,3,5-triazine hydrochloride on rat pancreatic islets, two doses of the compound (100 µM and 1 mM) were added to the medium 1-hour prior to a 24-hour incubation with or without a cocktail of rat cytokines (TNF-alpha, IL-1beta and INF-gamma). The conditions without cytokines allowed the analysis of the specific effect of the compound on islets while the combination of the drug with cytokines allowed the study of the effect of Imeglimin on islets under an inflammatory stress. To measure cell death in islets, quantification of cytoplasmic nucleosomes in islet cells, a consequence of DNA fragmentation during apoptosis (Robertson et al., 2000), was performed. To be able to compare the results with a double reference, the level of cell death in untreated islets but also in islets incubated only with cytokines was analyzed. Furthermore, a negative control and a positive control were added to the conditions with and without cytokines to test the effectiveness of the protocol. Cyclosporine A, reported to be toxic in pancreatic islets (Hahn et al., 1986) but protective in other cell types (Tharakan B. et al., 2009; Fauvel H. et al., 2002; Sullivan P. G. et al., 2000), was selected as the negative control while Exendin-4, with potent protective properties against cell death (Li et al., 2003; Wang and Brubaker, 2002), was used as the internal positive control. The results of the quantification of cell death for each condition are presented on FIG. 1.

For conditions without cytokine addition, (+)-2-amino-3,6-dihydro-4-dimethylamino-6-methyl-1,3,5-triazine hydro- Example 2

Compositions According to the Invention

Formulation 1:
(+)-2-amino-3,6-dihydro-4-dimethylamino-6-methyl-1,3,5-triazine hydrochloride: 1000 mg
microcrystalline cellulose: 114 mg
croscarmellose: 30 mg
polyvinylpyrrolidone: 40 mg
magnesium stearate: 15 mg
Opadry®: 25 mg
Formulation 2:
(+)-2-amino-3,6-dihydro-4-dimethylamino-6-methyl-1,3,5-triazine hydrochloride: 750 mg
microcrystalline cellulose: 110 mg
croscarmellose: 21 mg
polyvinylpyrrolidone: 30 mg
magnesium stearate: 10.5 mg
Opadry®: 20 mg
Formulation 3:
(+)-2-amino-3,6-dihydro-4-dimethylamino-6-methyl-1,3,5-triazine hydrochloride: 1000 mg
microcrystalline cellulose: 150 mg
croscarmellose: 25 mg
polyvinylpyrrolidone: 45 mg
magnesium stearate: 10 mg
Eudragit®: 25 mg.

The invention claimed is:

1. A method for protecting beta cells from cellular death to thereby delay the onset of type 1 diabetes, comprising administering to a patient in need thereof who is at risk of developing type 1 diabetes due to the presence of antibodies characteristic of the disease but who does not have all the symptoms of type 1 diabetes, an effective amount of a triazine derivative selected in the group consisting of 2-amino-3,6-dihydro-4-dimethylamino-6-methyl-1,3,5-triazine, a racemic form, tautomer, enantiomer, diastereoisomer and epimer thereof, and a pharmaceutically acceptable salt thereof thereby delaying the onset of type 1 diabetes by protecting beta cells from cellular death, said patient not having been administered insulin in a range of less than 24 hours before or after administration of the triazine derivative.

2. The method according to claim 1, wherein the triazine derivative is selected in the group consisting of (+)-2-amino-3,6-dihydro-4-dimethylamino-6-methyl-1,3,5-triazine and a pharmaceutically acceptable salt thereof.

3. The method according to claim 1, wherein the triazine derivative is selected in the group consisting of (−)-2-amino-3,6-dihydro-4-dimethylamino-6-methyl-1,3,5-triazine and a pharmaceutically acceptable salt thereof.

4. The method according to claim 2, wherein the pharmaceutically acceptable salt is hydrochloride.

5. The method according to claim 1, wherein the triazine derivative is the only administered active compound.

\* \* \* \* \*